United States Patent [19]

Bonicolini et al.

[11] Patent Number: 5,045,234

[45] Date of Patent: Sep. 3, 1991

[54] SOLUTION FOR CONTROLLING THE PERFORMANCE OF THE IONIC EXCHANGE CHROMATOGRAPHY COLUMN OF HPLC (HIGH PERFORMANCE LIQUID CHROMATOGRAPHY) APPARATUSES, AND A PROCESS FOR PREPARING THE SAME

[75] Inventors: Francesco Bonicolini, Monte San Savino; Umberto Basagni, Arezzo, both of Italy

[73] Assignee: A. Menarini S.A.S., Florence, Italy

[21] Appl. No.: 193,734

[22] Filed: May 12, 1988

[30] Foreign Application Priority Data

May 18, 1987 [IT] Italy .............................. 47948 A/87

[51] Int. Cl.[5] .............................. G01N 30/96
[52] U.S. Cl. .................................. 252/408.1; 436/15; 252/1
[58] Field of Search ................. 436/15; 252/408.1, 1

[56] References Cited

U.S. PATENT DOCUMENTS 3,977,995  8/1976  Louderback et al. .
4,248,634  2/1981  Forester .
4,250,051  2/1981  Armstrong .
4,260,516  4/1981  Moore .
4,448,888  5/1984  Bleile et al. .
4,465,774  8/1984  Huang et al. .
4,590,164  5/1986  Gain .

FOREIGN PATENT DOCUMENTS 8100913  4/1981  World Int. Prop. O. .

OTHER PUBLICATIONS

Delgado et al., Clinical Chemistry, vol. 27, No. 2, pp. 358-359 (1981).
Ellis, G. et al., Clinical Chemistry, vol. 30, No. 11, pp. 1746-1752 (1984).

Primary Examiner—Matthew A. Thexton
Assistant Examiner—Valarie Denise Fee
Attorney, Agent, or Firm—Brumbaugh, Graves, Donohue & Raymond

[57] ABSTRACT

The invention relates to a solution for controlling the performance of the ionic exchange chromatography column of HPLC apparatuses, and more particularly of the AUTO A1C HA 8110-8111 apparatus with a MICROPEARL S-F-W-A1C column, said solution being made up of a lyophilic hemolysate comprising hemoglobin, monobasic potassium phosphate, dibasic potassium phosphate, α-D-ribose, guanine, cytosine, thymine and uracil, and a solvent, for restoring the lyophilic hemolysate, comprising a nonionic surface active agent such as TRITON X-100, a bacteriostatic agent, such as for instance sodium azide, and water, and it also relates to a process for the production of said solution.

12 Claims, 2 Drawing Sheets

SOLUTION FOR CONTROLLING THE PERFORMANCE OF THE IONIC EXCHANGE CHROMATOGRAPHY COLUMN OF HPLC (HIGH PERFORMANCE LIQUID CHROMATOGRAPHY) APPARATUSES, AND A PROCESS FOR PREPARING THE SAME

The present invention relates to a solution for controlling the performance of the ionic exchange chromatography column of HPLC apparatuses, as well as to a process for the preparation of said solution. More particularly, this invention relates to a lyophilic hemolysate obtained from washed red blood corpuscles, and restored by means of a suitable solvent, for controlling the analytical system which is capable of determining the glycate hemoglobin HbA1C with the HPLC method by means of the device of the DAICHI company which is called "AUTO A1C HA 8110-8111", with a column of the MICROPEARL S-F-W-A1C, so that the results obtained are always reliable and do not undergo changes due to the decay of the separation column.

The column of the AUTO A1C HA 8110-8111 device, according to the manufacturing company of the HPLC apparatus, is capable of working on about 1000 samples.

On the contrary, a lower yield is obtained in many instances, due to losses of accuracy in the analytical determination, so that it is necessary to have at disposal a so-called "reference control samples".

Various control hemolysates are commercially available at the present time, which satisfy at a high degree the needs of the particular column of the HPLC apparatus for which they have been prepared.

On the contrary, said control hemolysates which are already available damage the column of the AUTO A1C HA 8110-HA 8111 device, making its average useful life shorter.

Moreover, such control samples, once they have been restored, have not an optimal dilution for the apparatus in question, so that they are to be adjusted before being processed.

In addition, some of the control samples commercially available at the present time, when subjected to analyses, show, if they are employed on a MICROPEARL column, anomalous separation peaks with respect to peaks obtained with the normal laboratory routine.

More particularly, the lyophilization process carried out without suitable measures causes a decay of hemoglobin that shows, when analyzing the sample with HPLC, with a remarkable increase in the so-called "a+b" fraction which gives such standard a number of features different from those of the normal control samples.

BRIEF DESCRIPTION OF THE DRAWING

Such effect is particularly evident if the FIGS. 1, 2 and 3 are observed, said figures showing, respectively, the plots of the results obtained employing on the HPLC apparatus a control standard commercially available, and the results obtained analyzing routine samples in a physiologic and in a pathologic patient.

Figure 1:
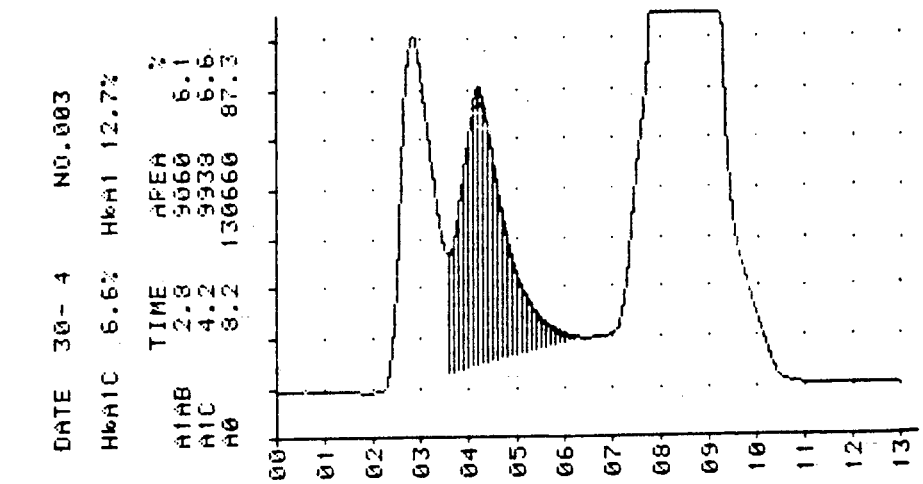
Figure 2:
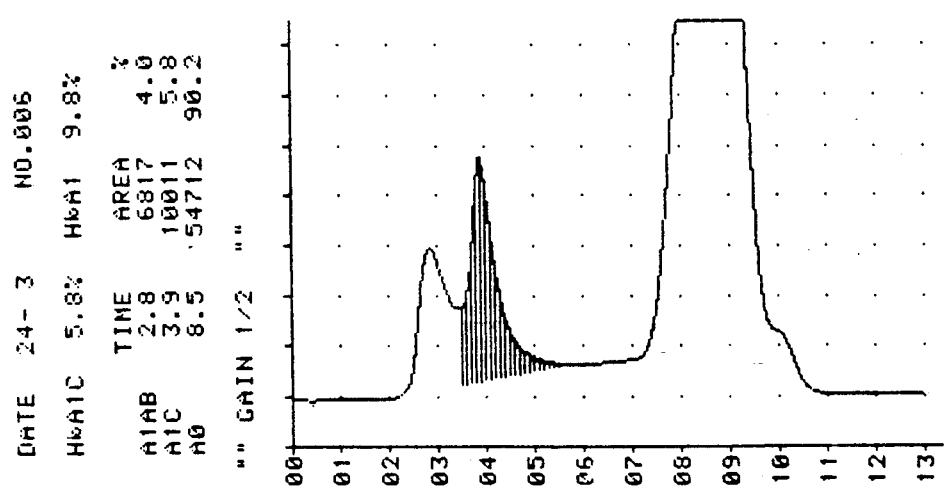
Figure 3:
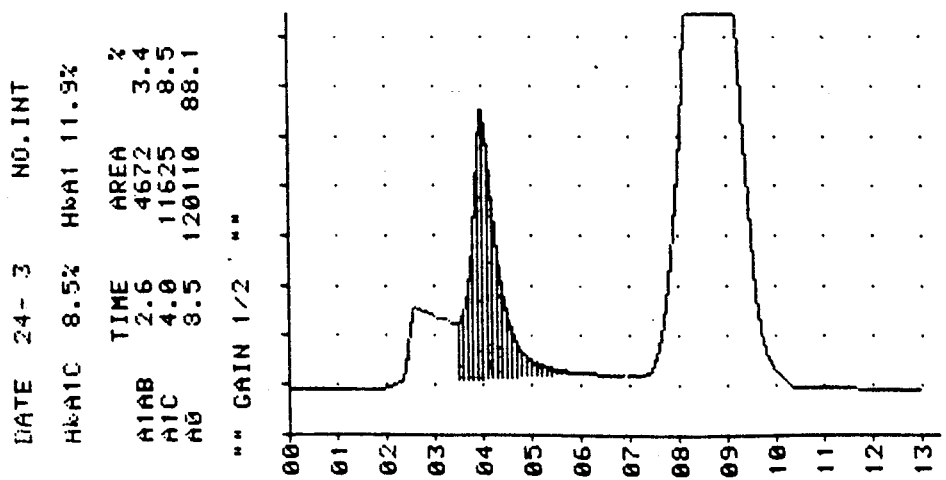
Figure 4:
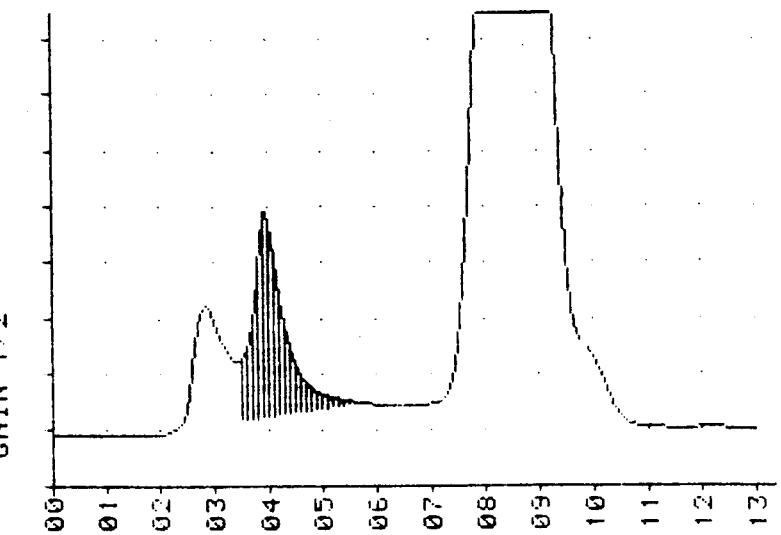
FIGS. 4 and 5 show the plots obtained employing the control solution according to the present invention respectively in the case of physiologic and pathologic valves.
Figure 5:
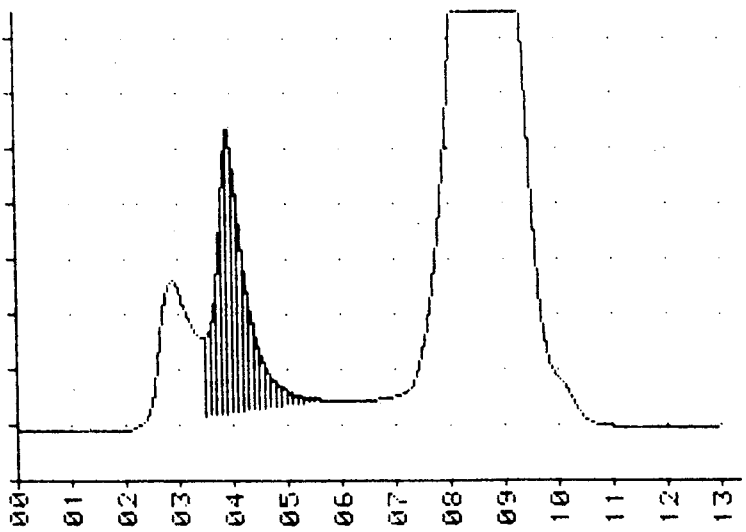

Thus, the lack derives from the above of what is to be considered as the main feature of a control standard: i.e., a behaviour as similar as possible to the behaviour of a routine sample.

According to the above, it is quite evident that it is very important to have at disposal a control solution such as that suggested by the applicant, which solves the problems mentioned above suggesting the realization of a solution of the type mentioned for monitoring the AUTO A1C device.

Another object of the present invention is the realization of a control solution as mentioned above which is characterized by a high dilution of the red blood cells in the lyophilic hemolysate, about 1 cc of red cells/50 ml of the buffer solution, so that a high number of vials can be prepared with a very small amount of blood.

A further object of the invention is the realization of a control solution that is obtainable employing animal blood in general.

Accordingly, it is a specific object of the present invention to provide a solution for controlling the performance of the ionic exchange chromatography column of HPLC (High Performance Liquid Chromatography) apparatuses, and in particular of AUTO A1C HA 8110-8111 apparatuses with MICROPEARL S-F-W-A1C columns, said solution being made up of a lyophilic hemolysate comprising hemoglobin in amounts of $8.0 \times 10^{-4}$ g ($\pm 50\%$), monobasic potassium phosphate in amounts of $9 \times 10^{-4}$ g ($\pm 50\%$), dibasic potassium phosphate in amounts of $3 \times 10^{-4}$ g ($\pm 50\%$), as well as of a solvent comprising a nonionic surface active agent in amounts of $1.5 \times 10^{-3}$ g ($\pm 50\%$), sodium azide in amounts of $3 \times 10^{-4}$ g ($\pm 50\%$), and water in amount of 1.5 ml.

Said lyophilic hemolisate of the solution according to the present invention can comprise α-D-ribose in amounts of $2.5 \times 10^{-6}$ g ($\pm 50\%$) and preferably of $2.5 \times 10^{-6}$ g.

Again according to the present invention, said lyophilic hemolysate can also contain at least one of the bases cytosine, thymine, guanine and uracil, in such amounts as to contain a total of $4.7 \times 10^{-4}$ ($\pm 50\%$) micromoles.

Preferably, at least two bases will be present, selected from among cytosine, guanine, thymine and uracil, in such amounts that the total amount contained is within the limits mentioned above.

According to a preferred embodiment of the solution of the present invention, said lyophilic hemolizate contains cytosine in amounts of $1.35 \times 10^{-4}$ ($\pm 50\%$) micromoles, guanine in amounts of $0.94 \times 10^{-4}$ ($\pm 50\%$) micromoles, thymine in amounts of $0.93 \times 10^{-4}$ ($\pm 50\%$) micromoles, and uracil in amounts of $1.49 \times 10^{-4}$ ($\pm 50\%$) micromoles.

Further according to the present invention said nonionic surface active agent consists of TRITON (Registered Trade Mark) X-100 i.e., polyethylene glycol alkyl aryl ether in amounts of $1.5 \times 10^{-3}$ g ($\pm 50\%$), and preferably of $1.5 \times 10^{-3}$ g, while sodium azide is present in amount of $3 \times 10^{-4}$ g.

A composition of the control solution according to the present invention which is particularly preferred comprises a lyophilic hemolysate that is made of:

$8 \times 10^{-4}$ g of hemoglobin;
$9 \times 10^{-4}$ g of monobasic potassium phosphate;
$3 \times 10^{-4}$ g of dibasic potassium phosphate;
$2.5 \times 10^{-6}$ g of α-D-ribose;
$0.94 \times 10^{-4}$ micromoles of guanine;

$1.35 \times 10^{-4}$ micromoles of cytosine;
$0.93 \times 10^{-4}$ micromoles of thymine;
$1.49 \times 10^{-4}$ micromoles of uracil;
and a solvent which consists of:
$1.5 \times 10^{-3}$ g of TRITON X-100;
$3 \times 10^{-4}$ g of sodium azide;
1.5 ml of water.

The presence of the surface active agent and of the bacteriostatic agent serves the purpose of dissolving the stromata that are formed in the lyophilic hemolysate.

Moreover, the scope of the present invention also contemplates a process for the preparation of the control solution disclosed above, said process comprising the steps of:
treating the whole blood with an anti-coagulating agent;
centrifuging at 150 G for ten minutes;
removing the plasma;
adding a physiologic solution in amounts between 4 and 10 ml;
centrifuging;
repeating the centrifugation till a clear supernatant is obtained;
suspending the red blood cells in the physiologic solution for 24 hours;
centrifuging and removing the top part, so obtaining the red blood cells washed;
preparing the stabilizing solution;
adding 50 microliters of said solution for each ml of the red blood cells and homogenizing the whole mass gently;
diluting the red blood cells+stabilizing solution at a ratio of 1/50 into a solution of monobasic potassium phosphate, dibasic potassium phosphate and water;
keeping at rest for about 60 minutes;
filling the solution into small vials and putting the same into the freeze-drying apparatus till a moisture less than 2% is obtained;
restoring the lyophilic hemolysate so obtained with a solution of a nonionic surface active agent, a bacteriostatic agent and water.

PREPARATION EXAMPLE 10 ml of whole blood treated with an anti-coagulating agent are centrifuged at 150 G for 10 minutes.

Then the plasma is removed.

5 ml of physiologic solution is then added and the whole mass is centrifuged.

The operation is repeated till a clear supernatant is obtained.

The erythrocytes are then suspended in the physiologic solution for 24 hours.

The mass is centrifuged again and the top part is removed. Thus the washed erythrocytes are obtained as the residue.

Separately the stabilizing agent is prepared, which consists of:

α-D-ribose: 10 g
cytosine: 0.060 g
guanine: 0.057 g
thymine: 0.047 g
uracil: 0.067 g
water: q.s. to 1 l 50 microliters of that solution is added for each ml of red cells.

The red blood cells are then homogenized with the solution gently and then they are diluted (erythrocytes+stabilizing) in the ratio 1/50 with a solution of 3.600 g of $KH_2PO_4$, 1.2 g of $K_2HPO_4$ and water q.s. to 1 l.

As a result, the erythrocytes become hemolyzed with liberation of hemoglobin.

The material is kept at rest for 60 minutes, then it is filled into small vials with 0.250 ml, and the vials are put into the freeze-drying unit till the obtainment of a moisture content less than 2%.

For employment, the lyophilic hemolysate is restored with 1.5 ml of a solution consisting of TRITON (Registered Trade Mark) X-100 (1.0 g), $NaN_3$ (2.0 g) and water q.s. to 1 l.

The present invention has been disclosed according to some preferred embodiments of the same, but it is to be understood that modifications and/or changes can be introduced in the same by those who are skilled in the art without departing from the spirit and scope of the invention for which a priority right is claimed.

What is claimed is:

1. A solution for controlling the performance of the ionic exchange chromatography column of a HPLC apparatus, said solution comprising
   (a) a lyophilic hemolysate comprising
      (1) hemoglobin in the amount of from $4.0 \times 10^{-4}$ g to $12.0 \times 10^{-4}$ g;
      (2) monobasic potassium phosphate in the amount of from $4.5 \times 10^{-4}$ g to $13.5 \times 10^{-4}$ g;
      (3) dibasic potassium phosphate in the amount of from $1.5 \times 10^{-4}$ g to $4.5 \times 10^{-4}$ g;
      (4) α-D-ribose in the amount of from $1.25 \times 10^{-6}$ g to $3.75 \times 10^{-6}$ g; and
      (5) at least one base selected from the group consisting of cytosine, guanine, thymine and uracil, in an amount totalling from $2.35 \times 10^{-4}$ to $7.05 \times 10^{-4}$ micromoles; and
   (b) a solvent comprising
      (1) nonionic surface active agent in the amount of from $0.75 \times 10^{-3}$ g to $2.25 \times 10^{-3}$ g;
      (2) sodium azide in the amount of from $1.5 \times 10^{-4}$ g to $4.5 \times 10^{-4}$ g; and
      (3) water in the amount of 1.5 ml.

2. The solution according to claim 1, wherein the α-D-ribose is present in the amount of $2.5 \times 10^{-6}$ g.

3. The solution according to claim 1, wherein the solution comprises at least two bases selected from the group consisting of cytosine, guanine, thymine, and uracil.

4. The solution according to claim 3, wherein the solution comprises:
   cytosine in the amount of from $0.67 \times 10^{-4}$ to $2.025 \times 10^{-4}$ micromoles;
   guanine in the amount of from $0.47 \times 10^{-4}$ to $1.41 \times 10^{-4}$ micromoles;
   thymine in the amount of from $0.465 \times 10^{-4}$ to $1.395 \times 10^{-4}$ micromoles; and
   uracil in the amount of from $0.745 \times 10^{-4}$ to $2.235 \times 10^{-4}$ micromoles.

5. The solution according to claim 1, wherein the nonionic surface active agent is polyethylene glycol alkyl aryl ether.

6. The solution according to claim 1, wherein the solution comprises $1.5 \times 10^{-3}$ g of polyethylene glycol alkyl aryl ether and $3 \times 10^{-4}$ g of sodium azide.

7. A solution for controlling the performance of the ionic exchange chromatography column of a HPLC apparatus, said solution comprising:
(a) a lyophilic hemolysate comprising:
  (1) hemoglobin in the amount of $8 \times 10^{-4}$ g,
  (2) monobasic potassium phosphate in the amount of $9 \times 10^{-4}$ g,
  (3) dibasic potassium phosphate in the amount of $3 \times 10^{-4}$ g,
  (4) α-D-ribose in the amount of $2.5 \times 10^{-6}$ g,
  (5) cytosine in the amount of $1.3 \times 10^{-4}$ micromoles,
  (6) guanine in the amount of $0.94 \times 10^{-4}$ micromoles,
  (7) thymine in the amount of $0.93 \times 10^{-4}$ micromoles, and
  (8) uracil in the amount of $1.49 \times 10^{-4}$ micromoles; and
(b) a solvent comprising
  (1) polyethylene glycol alkyl aryl ether in the amount of $1.5 \times 10^{-3}$ g,
  (2) sodium azide in the amount of $3 \times 10^{-4}$ g, and
  (3) water in the amount of 1.5 ml.

8. A process for the preparation of a solution for controlling the performance of the ionic exchange chromatography column of a HPLC apparatus, said process comprising the steps of:
treating whole blood with an anti-coagulating agent;
centrifuging the treated blood to separate cells from a plasma supernatant;
removing the plasma supernatant and adding a physiologic solution to the cells;
repeating the centrifugation step until a clear supernatant is obtained;
suspending the final cell preparation in physiologic solution for approximately 24 hours;
centrifuging to separate the cells from the physiological solution;
removing the supernatant so as to leave washed erythrocytes behind;
adding 50 microliters of an aqueous stabilizing agent for each one (1) ml of washed erythocytes to form an erthrocyte solution, said stabilizing agent comprising α-D-ribose and at least one base selected from the group consisting of cytosine, guanine, thymine and uracil;
gently homogenizing said erythrocyte solution;
diluting the homogenized solution to the ratio of about 1:50 with a solution of monobasic potassium phosphate, dibasic potassium phosphate and water;
keeping the diluted solution at rest for approximately 60 minutes;
filling the diluted solution into a plurality of vials;
placing the vials into a freeze-drying unit until a lyophilic hemolysate with a moisture content of less than 2% is obtained; and
restoring the obtained lyophilic hemolysate with a restoring solution comprising a nonionic surface active agent, a bacteriostatic agent and water.

9. The process according to claim 8, wherein the nonionic surface active agent is polyethylene glycol alkyl aryl ether and the bacteriostatic agent is sodium azide.

10. The process according to claim 9, wherein the following components are used in the following relative amounts:
whole blood in the amount of 10 ml;
physiologic solution between 4 and 10 ml;
stabilizing agent comprising
  α-D-ribose in the amount of 10 g,
  cytosine in the amount of 0.060 g,
  guanine in the amount of 0.057 g,
  thymine in the amount of 0.047 g,
  uracil in the amount of 0.067 g, and
  water q.s. to 1 liter;
solution of monobasic and dibasic potassium phosphate and water comprising
  $KH_2PO_4$ in the amount of 3.6 g,
  $K_2HPO_4$ in the amount of 1.2 g, and
  water q.s. to 1 liter;
1.5 ml of the restoring solution comprising
  polyethylene glycol alkyl aryl ether in the amount of 1.0 g,
  sodium azide in the amount of 2.0 g, and
  water q.s. to 1 liter.

11. The process according to claim 10, wherein the physiologic solution is used in the amount of 5 ml.

12. The process according to claim 10, wherein the vials have a capacity of approximately 0.25 ml.

* * * * *